United States Patent
Anderson et al.

(10) Patent No.: US 8,079,498 B2
(45) Date of Patent: Dec. 20, 2011

(54) HOLDER FOR A SPRAY CONTAINER

(75) Inventors: James Anderson, Hull (GB); Wu Jin, Hull (GB); Simon Woolley, Hull (GB); Ivan Ye, Hull (GB)

(73) Assignee: Reckitt Benckiser (UK) Limited, Slough, Berkshire (GB)

( * ) Notice: Subject to any disclaimer, the term of this patent is extended or adjusted under 35 U.S.C. 154(b) by 828 days.

(21) Appl. No.: 11/816,050

(22) PCT Filed: Feb. 2, 2006

(86) PCT No.: PCT/GB2006/000342
§ 371 (c)(1),
(2), (4) Date: Oct. 30, 2007

(87) PCT Pub. No.: WO2006/087514
PCT Pub. Date: Aug. 24, 2006

(65) Prior Publication Data
US 2008/0061082 A1 Mar. 13, 2008

(30) Foreign Application Priority Data
Feb. 15, 2005 (GB) ................... 0503095.2

(51) Int. Cl.
*B67D 7/06* (2010.01)
(52) U.S. Cl. ...................... 222/183; 239/333
(58) Field of Classification Search .............. 222/183, 222/187, 173, 182, 402.13, 171, 325–327, 222/1, 52, 645, 649, 504, 162, 402.1; 239/390–393, 239/333, 34; 422/186.07, 186.01
See application file for complete search history.

(56) References Cited

U.S. PATENT DOCUMENTS

| | | | |
|---|---|---|---|
| 1,751,261 A | 3/1930 | Wilson |
| 3,184,115 A | 5/1965 | Meshberg |
| 3,187,949 A | 6/1965 | Mangel |
| 3,225,782 A | 12/1965 | Bealey et al. |
| 3,250,444 A | 5/1966 | Ward |
| 3,358,889 A | 12/1967 | Robinson |
| 3,420,260 A | 1/1969 | Winsiniewski |
| 3,521,851 A | 7/1970 | Sorrow |
| 3,627,176 A | 12/1971 | Sailors |
| 3,666,144 A | 5/1972 | Winder |
| 3,732,509 A | 5/1973 | Florant et al. |
| 3,848,775 A | 11/1974 | Possell |
| 3,972,473 A | 8/1976 | Harrison |
| 3,974,941 A | 8/1976 | Mettler |
| 3,985,333 A | 10/1976 | Paulsen |
| 4,006,841 A | 2/1977 | Alticosalian |
| 4,077,542 A | 3/1978 | Petterson |

(Continued)

FOREIGN PATENT DOCUMENTS

DE 1491714 A1 5/1969
(Continued)

*Primary Examiner* — Lien Ngo
(74) *Attorney, Agent, or Firm* — Norris McLaughlin & Marcus PA

(57) ABSTRACT

A sleeve (10) for a material container (14), the sleeve being adapted to receive a material container (14) therein, the sleeve also being adapted to be received in an opening of a corresponding material ejection device chassis (12) operable to control ejection of material from the material container (14), wherein the sleeve (10) includes a magnet (42) operable to activate an electromagnetic switch of the material ejection device chassis (12).

15 Claims, 6 Drawing Sheets

U.S. PATENT DOCUMENTS

| | | | |
|---|---|---|---|
| 4,310,125 A | 1/1982 | Novotny | |
| 4,454,963 A | 6/1984 | Fegley | |
| 4,515,345 A | 5/1985 | Inden et al. | |
| 4,643,359 A | 2/1987 | Casey | |
| 4,871,989 A | 10/1989 | Gross | |
| 4,877,989 A | 10/1989 | Drews et al. | |
| 4,884,720 A | 12/1989 | Whigham et al. | |
| 4,889,284 A | 12/1989 | Spector | |
| 4,962,340 A | 10/1990 | Isozumi | |
| 4,969,584 A | 11/1990 | Joulia | |
| 5,015,980 A | 5/1991 | Sugiyama | |
| 5,025,962 A | 6/1991 | Renfro | |
| 5,027,846 A | 7/1991 | Baron | |
| 5,085,402 A | 2/1992 | O'Dell | |
| 5,150,842 A | 9/1992 | Hickey | |
| 5,178,354 A | 1/1993 | Engvall | |
| 5,221,025 A * | 6/1993 | Privas | 222/1 |
| 5,358,147 A * | 10/1994 | Adams et al. | 222/183 |
| 5,417,373 A | 5/1995 | Facchin | |
| 5,427,277 A | 6/1995 | Bierend et al. | |
| 5,447,273 A | 9/1995 | Wozniak | |
| 5,505,195 A | 4/1996 | Wolf et al. | |
| 5,598,142 A | 1/1997 | Winner, Jr. | |
| 5,603,433 A | 2/1997 | Rene | |
| 5,606,992 A | 3/1997 | Erickson et al. | |
| 5,685,459 A | 11/1997 | Wardle | |
| 5,791,520 A | 8/1998 | Tichenor | |
| 5,875,934 A * | 3/1999 | Miller et al. | 222/183 |
| 5,895,318 A * | 4/1999 | Smrt | 454/256 |
| 5,996,628 A | 12/1999 | Najmolhoda et al. | |
| 6,050,543 A | 4/2000 | LaGreca et al. | |
| 6,149,126 A | 11/2000 | Krimmer et al. | |
| 6,188,926 B1 | 2/2001 | Vock | |
| 6,216,925 B1 | 4/2001 | Garon | |
| 6,267,297 B1 | 7/2001 | Contadini et al. | |
| 6,349,854 B1 | 2/2002 | Bierend et al. | |
| 6,419,122 B1 * | 7/2002 | Chown | 222/162 |
| 6,431,400 B1 | 8/2002 | O'Maley et al. | |
| 6,546,959 B2 | 4/2003 | Cross et al. | |
| 6,622,893 B2 | 9/2003 | Leone et al. | |
| 6,631,888 B1 * | 10/2003 | Prueter | 261/30 |
| 6,978,914 B2 | 12/2005 | Furner et al. | |
| 7,140,515 B2 * | 11/2006 | Cardwell et al. | 222/183 |
| 7,407,065 B2 * | 8/2008 | Hooks et al. | 222/1 |
| 7,779,245 B2 | 8/2010 | Bachmutsky et al. | |
| 2001/0033766 A1 | 10/2001 | Gueret | |
| 2002/0190477 A1 | 12/2002 | Leone et al. | |
| 2003/0132254 A1 | 7/2003 | Giangreco | |
| 2003/0205580 A1 | 11/2003 | Yahav | |
| 2004/0155056 A1 | 8/2004 | Yahav | |
| 2004/0251271 A1 | 12/2004 | Jackson et al. | |
| 2005/0067439 A1 | 3/2005 | Yahav | |
| 2005/0133752 A1 | 6/2005 | Purvines et al. | |
| 2005/0252930 A1 | 11/2005 | Contadini et al. | |
| 2005/0279854 A1 | 12/2005 | Martens et al. | |
| 2006/0060615 A1 | 3/2006 | McLisky | |
| 2006/0185002 A1 | 8/2006 | Bachmutsky et al. | |
| 2007/0181609 A1 | 8/2007 | Rymer | |
| 2007/0257130 A1 | 11/2007 | Butler et al. | |
| 2008/0099483 A1 | 5/2008 | Anderson et al. | |
| 2008/0156896 A1 | 7/2008 | Anderson et al. | |
| 2010/0237108 A1 | 9/2010 | Anderson et al. | |

FOREIGN PATENT DOCUMENTS

| | | |
|---|---|---|
| DE | 2515491 A1 | 10/1976 |
| DE | 2920824 A1 | 1/1980 |
| DE | 2841161 A1 | 4/1980 |
| DE | 3909381 A1 | 12/1990 |
| DE | 29905971 U1 | 7/1999 |
| DE | 19951632 A1 | 5/2005 |
| EP | 0294223 A2 | 12/1988 |
| EP | 0506356 A2 | 9/1992 |
| EP | 0641727 1 A | 10/1994 |
| EP | 0691269 A1 | 1/1996 |
| EP | 1076014 A2 | 7/2000 |
| EP | 1316514 A2 | 6/2003 |
| FR | 2632019 | 12/1989 |
| FR | 2813870 | 3/2002 |
| GB | 936027 | 9/1963 |
| GB | 2214891 A | 9/1989 |
| GB | 2248888 A | 4/1992 |
| GB | 2262452 A | 6/1993 |
| GB | 2313311 A | 11/1997 |
| JP | 10072072 | 3/1998 |
| WO | 9110607 A1 | 7/1991 |
| WO | 9519304 A1 | 7/1995 |
| WO | 9633946 A1 | 10/1996 |
| WO | 0119701 A1 | 3/2001 |
| WO | 0155009 A1 | 8/2001 |
| WO | 03045819 A1 | 6/2003 |
| WO | 03057594 A1 | 7/2003 |
| WO | 03104109 A1 | 12/2003 |
| WO | 2006005962 A1 | 1/2006 |
| WO | 2006087414 | 8/2006 |
| WO | 2006087515 | 8/2006 |
| WO | 2006087516 A1 | 8/2006 |
| WO | 2006130410 A2 | 12/2006 |
| WO | 2007132140 A1 | 11/2007 |

* cited by examiner

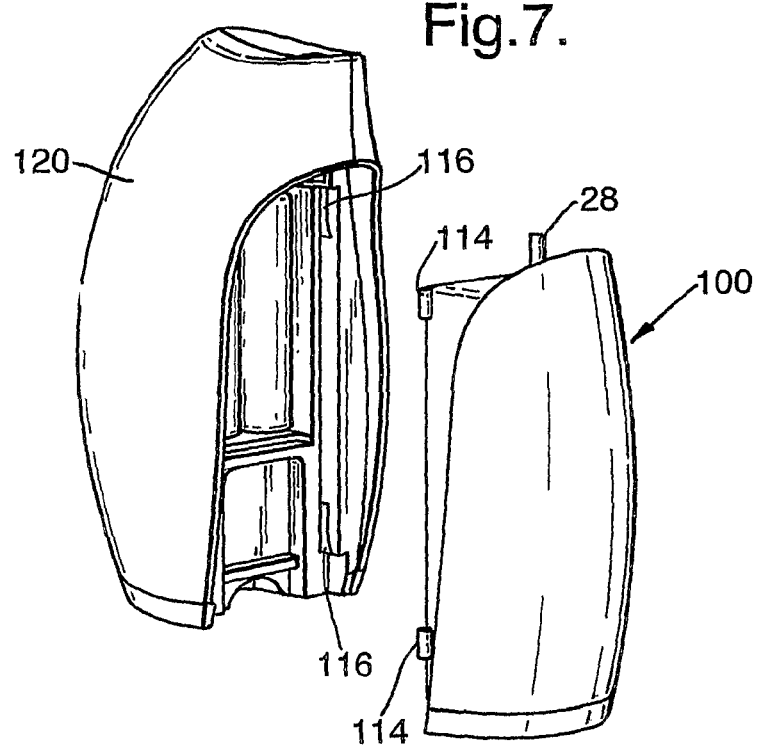
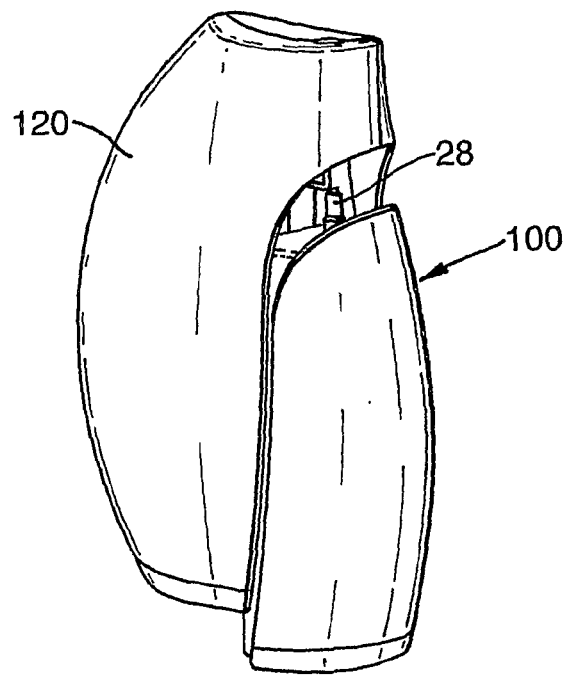

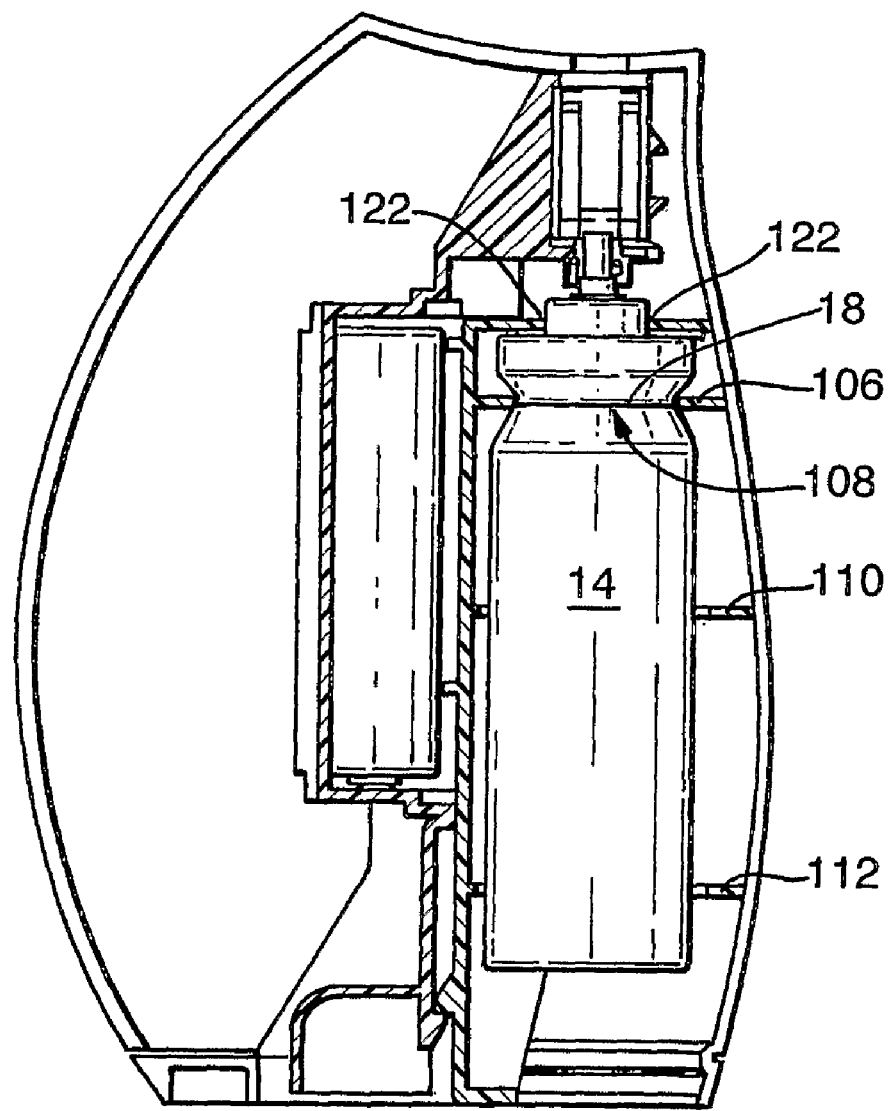

HOLDER FOR A SPRAY CONTAINER

This is an application filed under 35 USC 371 of PCT/GB2006/000342.

This invention relates to a holder, particularly, but not limited to, a holder for a spray container.

Devices for releasing fragrances, deodorants, sanitizing fluids, cleaning fluids, and the like in many cases utilise pressurised aerosol canisters. Such canisters typically release material upon depression of a tubular valve stem located at one end of the canister. The valve stem projects from a crimp section at an end of the canister, which crimp section typically has a narrowed waist section below a shoulder section.

Typically, two types of valve stem are used, a vertical action valve that uses an axial depression of the stem to activate the spray, and a tilt valve that is activated by depression of an arm that is pivoted to allow release of material.

The valve stem on a vertical action valve of an aerosol canister is prone to damage resulting from force applied to the valve stem in a direction other than that from which it is designed to receive a force. In normal use pressure should be applied to the valve stem along the axis of the stem. If force is applied at an angle to said axis then damage can result. Alternatively or additionally, misalignment of the valve stem on an element of a spray device through which material in the aerosol canister is to be dispensed can result in undesirable leaking of material from the aerosol canister. Such leaking of material is disadvantageous, particularly if the material held within the aerosol canister is caustic or difficult to remove in the event of spillage.

It is an object of the present invention to address the above mentioned disadvantages.

According to a first aspect of the present invention there is provided a sleeve for a material container, the sleeve being adapted to receive a material container therein, the sleeve also being adapted to be received in an opening of a corresponding material ejection device chassis operable to control ejection of material from the material container, wherein the sleeve includes a magnet operable to activate an electromagnetic switch of the material ejection device chassis.

The sleeve may comprise one of a locating projection and recess pair(s), the other of the locating projection and recess pair(s) being part of the material ejection device chassis. Throughout the specification, the word pair(s) refers to a single pair or to more than one such pair.

The sleeve may comprise material container gripping means, said material container gripping means comprising:
first gripping elements comprising tabs facing generally in a first direction and adapted to engage a neck section of the material container, and
second gripping elements adapted to extend over and adapted to engage a head section of the material container,
wherein the first and second gripping elements are adapted to provide a snap fitting for the material container and are adapted to bear against the neck section and head section of the material container respectively.

According to a second aspect of the invention there is provided a sleeve for a material container, the sleeve being adapted to receive a material container therein, the sleeve also being adapted to be received in an opening of a corresponding material ejection device chassis operable to control ejection of material from the material container, wherein the sleeve comprises one of a locating projection and recess pair(s), the other of locating projection and recess pair(s) being part of the material ejection device chassis.

The sleeve may comprise material container gripping means, said material container gripping means comprising:
first gripping elements comprising tabs facing generally in a first direction and adapted to engage a neck section of the material container, and
second gripping elements adapted to extend over and adapted to engage a head section of the material container,
wherein the first and second gripping elements are adapted to provide a snap fitting for the material container and are adapted to bear against the neck section and head section of the material container respectively.

The sleeve may include a magnet operable to activate an electromagnetic switch of the material ejection device chassis. The electromagnetic switch is preferably a reed switch.

According to a third aspect of the invention there is provided a sleeve for a material container, the sleeve being adapted to receive a material container therein, the sleeve also being adapted to be received in an opening of a corresponding material ejection device chassis operable to control ejection of material from the material container, wherein the sleeve incorporates material container gripping means, said material container gripping means comprising:
first gripping elements comprising tabs facing generally in a first direction and adapted to engage a neck section of the material container, and
second gripping elements adapted to extend over and adapted to engage a head section of the material container,
wherein the first and second gripping elements are adapted to provide a snap fitting for the material container and are adapted to bear against the neck section and head section of the material container respectively.

The gripping of the material container by the sleeve advantageously allows the sleeve to be inserted into the spray device chassis to achieve a desired alignment of an output section of the material container with a valve section or sealing assembly of the material ejection device chassis.

The sleeve may include a magnet operable to activate an electro-magnetic switch of the material ejection device chassis. The electromagnetic switch is preferably a reed switch.

The magnet may be a permanent magnet or other magnetisable body.

The magnet may be located on an upper part of the sleeve, preferably on the gripping means, more preferably on one of the second gripping elements. Preferably, the magnet is arranged so that the poles are generally aligned with a longitudinal axis of the sleeve.

The magnet is preferably located in a recess, which may be circular, preferably to match a disc-shape of the magnet. The magnet may be covered, which may be by an overmoulding process during manufacture.

Preferably, the magnet is located at or close to a vertex of the sleeve, for example at a shoulder thereof, to advantageously allow the magnet to approach the electromagnetic switch.

The sleeve may comprise one of a locating projection and recess pair(s), the other of the locating projection and recess pair(s) being part of the material ejection device chassis.

The sleeve preferably incorporates the locating projection(s), which is preferably at least one locating rib(s), which preferably extends along a body section of the sleeve, preferably from a shoulder section thereof. The locating projection(s) preferably extends to a base section, which is preferably wider than the body section.

The locating projection(s) preferably has a rounded profile, to preferably improve handling characteristics of the sleeve and/or to ease a moulding operation for production of the sleeve.

The base section preferably flares outwards from a base of the body section. The base section preferably includes at least one flexure slot adapted to allow flexure of the base section. Preferably more than one slot is provided to thereby form at least one flexure tab between the slots. The locating rib preferably extends from the shoulder section, along the body section and down to one of the flexure tabs.

The at least one flexure tab may include at least one locking projection/recess to lock into a corresponding recess/projection of the spray device chassis.

Preferably, the second gripping elements are joined at upper ends thereof by a link section, the latter preferably forming a ring adapted to engage the head section of the material container. The ring preferably has an opening adapted to allow an output stem section of the material container to project therethrough.

The second gripping elements and link section advantageously provide a firm hold to the head section to deter movement of the material container in the first direction. The first gripping means advantageously deters movement of the material container in a second direction. Thus, the first and second gripping means, in conjunction with the link section, advantageously hold the material container firmly in position with respect to the sleeve. The first and second directions are preferably directly away from one another, for example upwards and downwards.

The second gripping elements preferably consist of an upright section that is generally aligned with the longitudinal axis of the sleeve and an upper section that is approximately perpendicular to the longitudinal axis of the sleeve. Preferably the vertex close to which the magnet may be placed is the vertex between the upright and upper sections. The upper sections are preferably joined together by the link section.

The first gripping elements are each preferably located between two of the second gripping elements. Slots may form sides of the first gripping elements, said slots also forming sides of the second gripping elements. The slots may allow flexure of the first gripping elements.

The first gripping elements preferably have tapered ends, preferably formed by a cut-away section of an underside thereof. The cut-away section preferably provides a more gradual angle of approach for the material container as it is inserted into the sleeve.

The invention extends to a sleeve incorporating a material container.

The invention extends to a pack of sleeves incorporating material containers. The different material containers preferably contain different, preferably differently fragranced, materials therein.

All of the features described herein may be combined with any of the above aspects, in any combination.

For a better understanding of the invention, and to show how embodiments of the same may be carried into effect, reference will now be made, by way of example, to the accompanying diagrammatic drawings in which:

FIG. 7 is a schematic perspective view of the second embodiments of aerosol canister sleeve and spray device chassis separated from one another;

FIG. 8 is a schematic perspective view of the second embodiments of aerosol canister sleeve and spray device chassis partially engaged with one another;

FIG. 9 is a schematic cross-sectional side view of the second embodiment of aerosol canister sleeve engaged in the second embodiment of spray device chassis.

Aerosol spray devices are popular for dispersing fragrances, deodorising preparations and other materials. Such aerosol devices are becoming more complex as more control over the amount and timing and release of the material in the aerosol container is provided. With this increasing complexity comes a need for greater control over replacement aerosol canisters for the spray devices. The need for greater control arises because damage to the fragile stem of an aerosol canister can lead to malfunctioning of the spray device. Also, new devices in which a stem of aerosol canister must approach a sealing section of the spray device to provide a seal require good contact to be made between the end of the aerosol canister stem and the part of the spray device that receives the aerosol canister stem.

In such spray devices, such as those described in the applicant's co-pending patent application filed on the same date as the present application, a seal between the aerosol canister stem and a receiving part of the spray device prevents material from being released from the aerosol canister, rather than a valve within the aerosol canister, as is normally the case. In view of the sealing method used, the alignment of the aerosol canister stem and the spray device is a more important feature than has previously been the case.

The fragrances used in the spray devices described above may form a sticky residue if allowed to leak from the container, an increased advantage results if leaks can be prevented.

It is with these features and requirements in mind, that the applicant has developed a sleeve for placing over a spray material container such as an aerosol canister.

Figure 1:
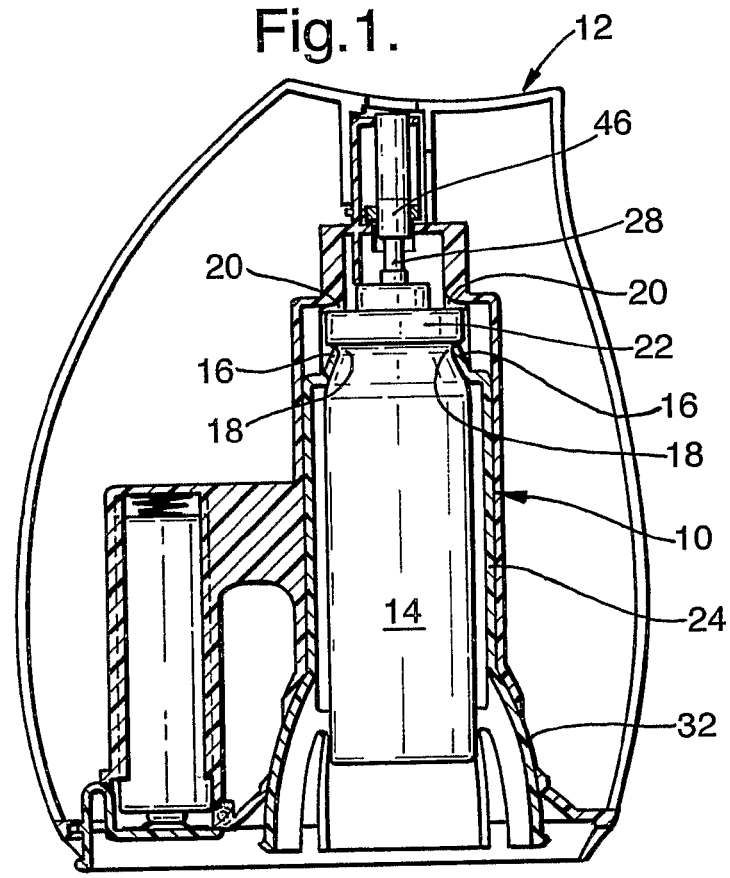
FIG. 1 is a schematic cross-sectional side view of an aerosol canister sleeve in position in a spray device chassis.

FIG. 1 shows an aerosol canister sleeve 10 located within a spray device chassis 12. The aerosol canister sleeve 10 holds an aerosol canister 14 in position by means of upwardly directed tabs 16 that engage a crimp section 18 of the aerosol canister 14. Four shoulder sections 20 of the aerosol canister sleeve 10 engage a head section 22 of the aerosol canister 14.

The four shoulder sections 20 are formed in the shape of strips (see FIG. 2) which extend from a main body 24 of the sleeve 10. The strip-shaped shoulder sections 20 extend upwards to a ring-shaped collar 26 which provides an opening through which a stem 28 of the aerosol canister 14 extends. The ring-shaped collar 26 provides beneficial strength to the sleeve 10 to deter undesirable upward movement of the canister 14.

The upwardly directed tabs 16 prevent downward movement of the aerosol canister 14 relative to the sleeve 10 and the shoulder sections 20 prevent upward movement of the aerosol canister 14 relative to the sleeve 10. In this way, the aerosol canister 14 is held firmly within the aerosol canister sleeve 10. Thus the firm holding of the canister aids the correct insertion of the sleeve 10 and its canister 14 into the spray device chassis 12. The aerosol canister 14 is inserted into the sleeve by being pushed upwards from below until the tabs 16 engage with the crimp section 18 by a snap fit. The aerosol canister 14 can be removed from the aerosol canister sleeve 10, but this results in breaking of the tabs 16 and so prevents re-use of the aerosol canister sleeve 10.

Figure 2:
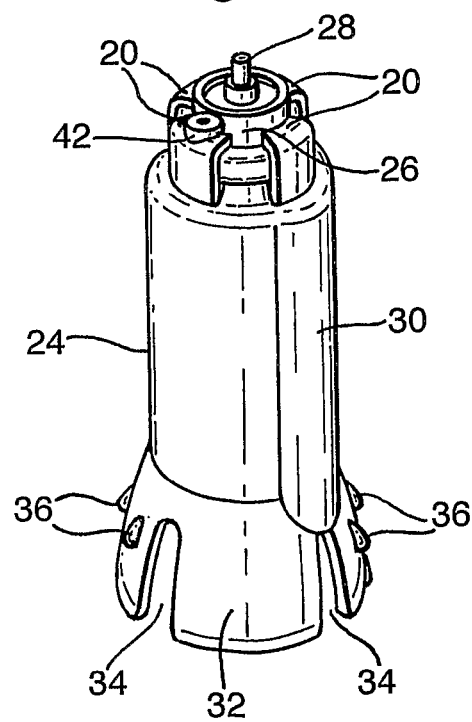
FIG. 2 is a schematic perspective view of the aerosol canister sleeve with an aerosol canister therein.
Figure 3:
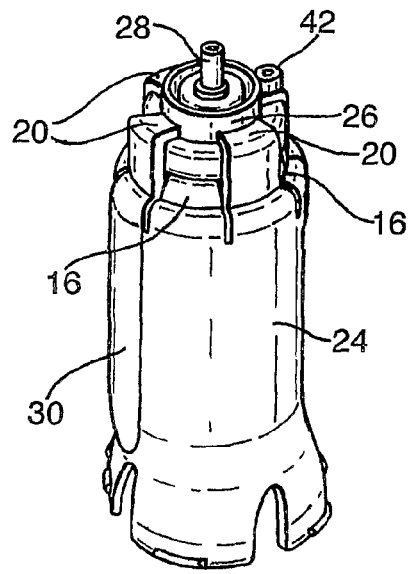
FIG. 3 is a schematic perspective view of the aerosol canister sleeve next to the spray device chassis.
Figure 4:
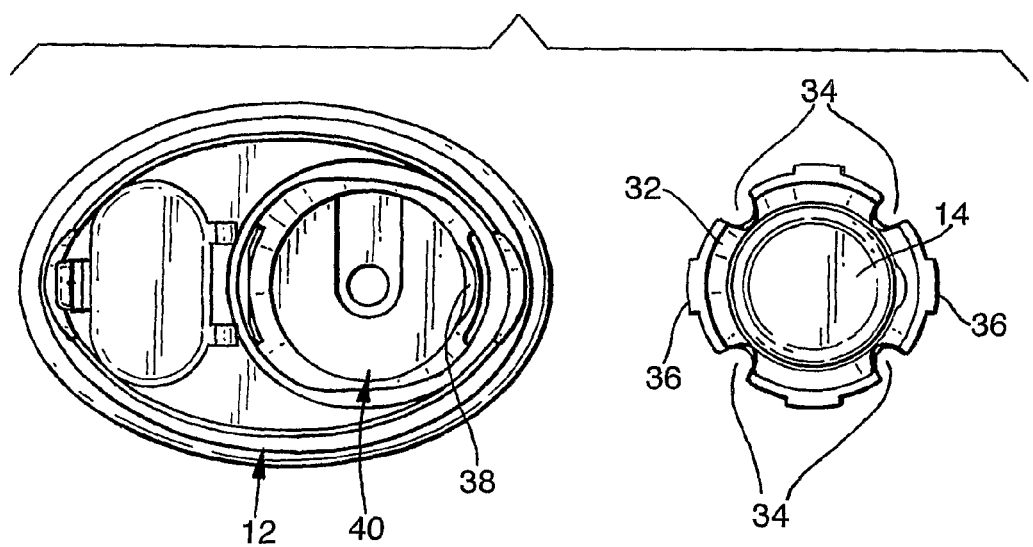
FIG. 4 is a schematic view from below of the aerosol canister sleeve containing an aerosol canister and a view from below of the spray device chassis.
Figure 5:
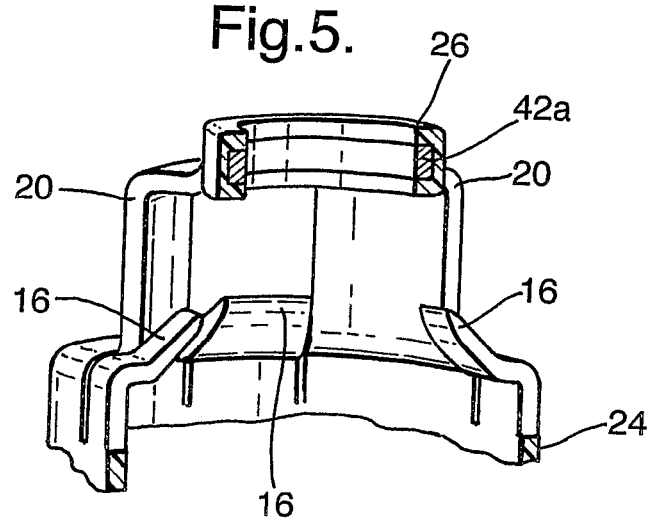
FIG. 5 is a schematic perspective cross-sectional view of a variant of the embodiment shown in FIGS. 1 to 4 of the aerosol canister sleeve.
Figure 6:
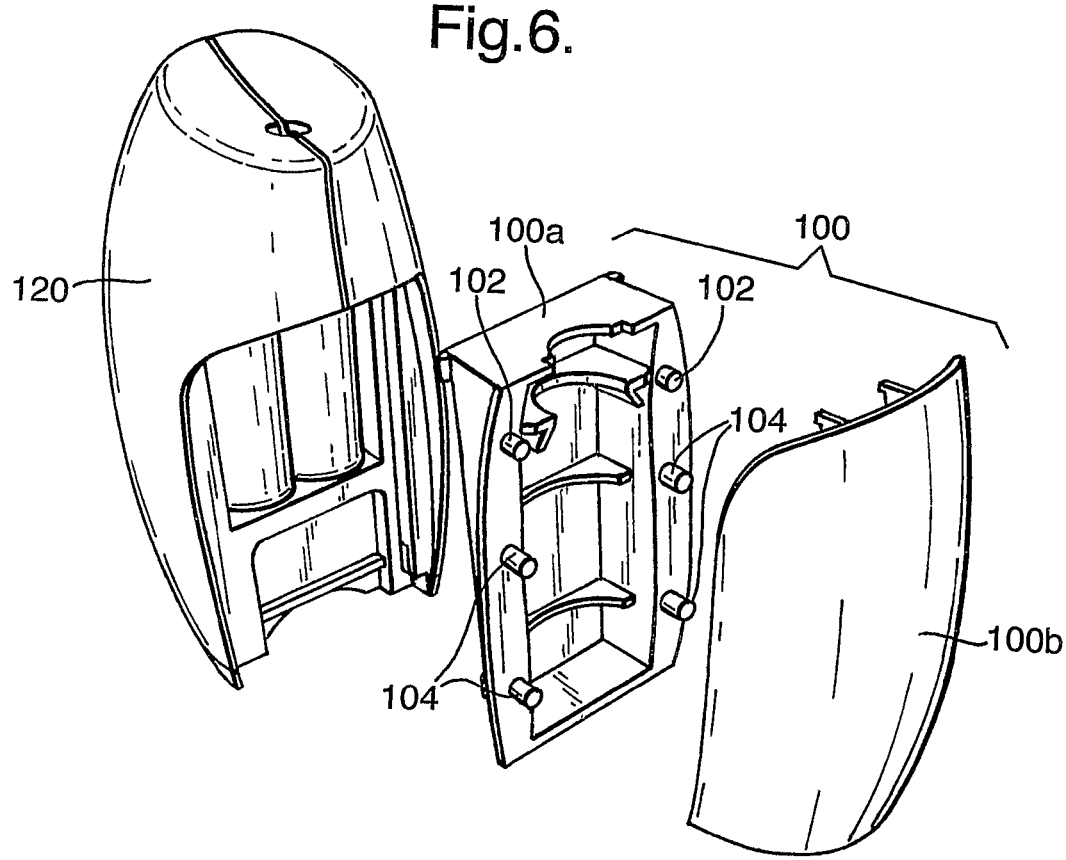
FIG. 6 is a schematic perspective view of a second embodiment of aerosol canister sleeve in a separated configuration, together with a second embodiment of spray device chassis.

As shown in FIG. 2 a rib 30 extends down the main body 24 of the sleeve 10 towards a flared base section 32. The rib 30 has a rounded profile, which makes the sleeve 10 easier to handle and easier to mould. In alternative embodiments there may be two or more such ribs on sleeve 10.

Slots 34 extend part way up the flared base section 32 from an open lower part of the flared base section 32. The slots 34 allow flexure of the flared base section 32 when squeezed by a user to disengage projections 36 which extend outwards from the flared base section 32 and are used to lock the aerosol canister sleeve 10 within the spray device chassis 12.

The rib 30 extends along the main body 24 of the sleeve 10 and may terminate between the slots 34 or as shown in FIG. 2. The shape and location of the rib 30 corresponds to the shape and location of a corresponding groove 38 in an opening 40 in the chassis 12 arranged to receive the aerosol canister sleeve 10. Where there is more than one rib 30, there is a corresponding number of grooves 38. The rounded profile of the rib(s) 30 and corresponding groove(s) 38 facilitate engagement with each other compared to angular ribs and grooves. The provision of the rib(s) 30 and the groove(s) 38 allows for correct relative location of the sleeve with respect to the chassis to ensure that the correct alignment of the sleeve 10 about a vertical axis thereof is achieved relative to the spray device chassis 12. The reason for requiring such an alignment is to ensure that a magnet 42 located on one of the shoulder sections 20 of the sleeve 10 is correctly located with respect to a reed switch 44 (see FIG. 1). Reed switches are described in more detail in the applicant's co-pending U.K. application. A reed switch is an electromagnetic switch that can be arranged to either open or close only in the presence of a magnet. In this case, the reed switch 44 is arranged to close in the presence of the magnet 42. Closure of the reed switch 44 allows a solenoid valve 46 of the spray device chassis 12 to receive power and periodically eject material from the aerosol canister 14 under control of control circuitry (not shown) of the spray device chassis 12. In order for the reed switch 44 to function, the magnet 42 must be within a sensing distance of the reed switch.

Thus, orientation of the aerosol canister sleeve 10 and more particularly the magnet 42, with respect to the spray device chassis 12 and more particularly the reed switch 44, is an important requirement of the aerosol canister sleeve 10 and the way it fits in to the spray device chassis 12. An alternative configuration would be to provide a magnet 42 on each of the four shoulders 20. However, it is found to be advantageous to provide only one magnet 42, which reduces the material and production costs of the aerosol canister sleeve 10.

The shoulders 20 of the aerosol canister sleeve 10 advantageously provide a suitable position for location of the magnet 42 on a generally horizontal upwardly facing surface, which allows a corresponding beneficial location of the reed switch 44 in a position easily accessible to the magnetic field of the magnet 42 within the spray device chassis 12.

The magnet 42 is located in a disc-shaped recess formed in the shoulder section 20, corresponding to a disc-shape of the magnet 42. The magnet 42 is held in position either by adhesive or by an interference fit in the pocket.

The magnet 42 may be hidden from view by an overmoulding process known in the moulding art, by which the magnet 42 is embedded during moulding beneath a layer of the plastics material used for the sleeve 10.

Alternatively the magnet 42 may be replaced by material that is magnetisable that is put in position during or after moulding and is subsequently magnetised before use.

The use of the sleeve 10 to provide a location for the magnet 42 to be used with the reed switch 44 has significant advantages over the alternative of simply securing a magnet 42 to the aerosol canister 14, because manufacture of the aerosol canister 14 is already underway in high volume and to change this manufacturing procedure would be disadvantageously costly. Consequently, the use of the sleeve 10, with the advantages referred to herein provides an efficient combination of advantages which would not previously have been envisaged as being achievable or useful in a simple sleeve. Alternatively the magnet 42 may be secured to the aerosol canister 14 directly.

In use, the shape of the aerosol canister sleeve 10 allows only one relative orientation of the sleeve 10 with the spray device chassis 12. Also, the sleeve provides a perpendicular approach of the stem 28 of the aerosol canister 14 to a surface of the solenoid (not shown). This prevents damage to an O-ring that forms part of the solenoid interface and evenly distributes actuation force on the sealing surface of the solenoid. These features are particularly important in a device such as this in which the internal valve of the aerosol canister 10 is not used, but instead a seal between the end of the stem 28 and the sealing surface of the solenoid is used to prevent leakage of the material held in the canister. The solenoid valve is actuated by means of the reed switch 44 and magnet 42 pair. Thus, the approach of the end of the stem 28 to the sealing surface of the solenoid switch is considerably more important than would previously been the case with prior art devices. The use of the sleeve 10 allows smooth engagement of the sleeve and its aerosol canister 14 with the spray device chassis 12. The projections 36 engage the chassis 12 to hold the sleeve 10 in position. Thus, there is easy and quick removal of the aerosol canister 14 in its sleeve 10 from the spray device chassis 12.

Other advantages result from use of the aerosol canister sleeve 10, which include a visual cue from the sleeve 10 by means of use of coloured plastic for the sleeve which matches that of the chassis 12, which visual cue indicates that the correct sleeve, and hence the correct aerosol canister 14, is being used with the spray device chassis 12. This feature is important when a particular formulation has been arrived at taking into account the particular performance characteristics of the spray device chassis 12 and in particular the solenoid valve 46. A formulation may be optimised, e.g. in terms of viscosity etc to function well within a specific chassis 12. The sleeve 10 is typically made of plastics material, the colour of which can be matched to the particular type of fragrance used.

A further advantage of the sleeve 10 described above is that different sizes of aerosol canister 14 can be used. For example, a shorter aerosol canister 14 could be inserted into the sleeve 10, which may suit particular purposes. Also, looking at FIG. 1, a longer aerosol canister 14 could be used. This advantage results from holding only a top section, i.e. the head section 22 and the crimp section 18 of the aerosol canister 14, with no holding of the main body of the aerosol canister 14. Instead, a relatively close fit of the aerosol canister 14 inside the main body 24 of the sleeve 10 is provided to prevent more than a small amount of relative movement of the aerosol canister 14 within the main body 24 of the sleeve 10. An alternative construction would be to have a short main body 24 that extended only a small distance below the crimp section 18 of the canister 14.

The presentation of an aerosol canister 14 in the sleeve 10 provides a reference for a consumer that the particular type of material held within the aerosol canister will function properly with the spray device chassis 12.

Also, the provision of the sleeve 10 addresses the safety issue of using an aerosol canister which is not approved or manufactured by the present applicant. In such a case material could leak from the non-approved canister, which material may potentially be flammable, if a seal is not produced correctly between the correct type of aerosol canister 14 and stem 28. A non-authorised canister may not have the correct stem to seal properly with the spray device chassis 12. The device or sleeve may also be made without using the reed switch/magnet pair, whilst still gaining some or all of the benefits mentioned above.

Figure 10:
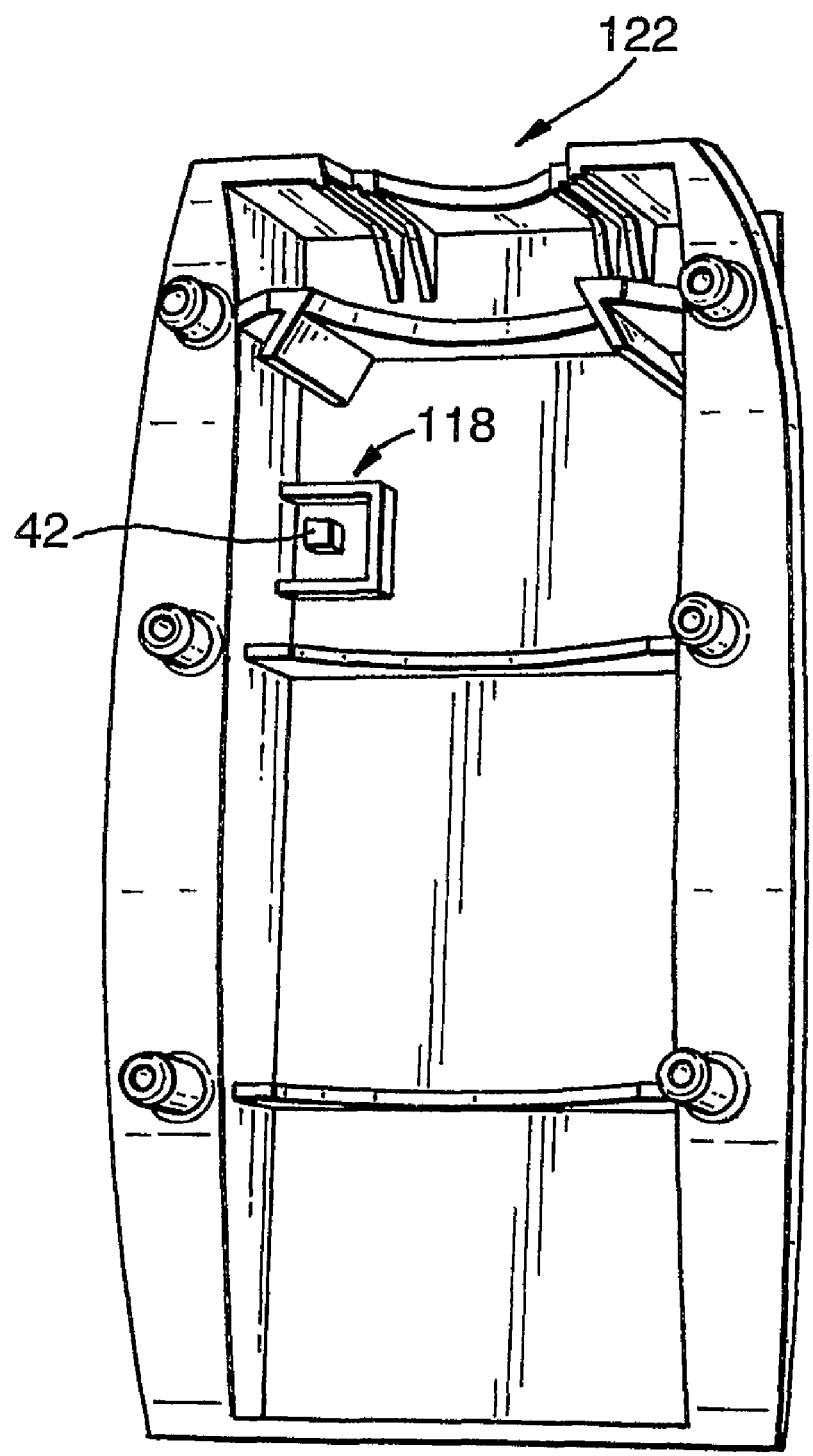
FIG. 10 is a perspective side view of a part of the second embodiment of aerosol canister sleeve.

FIGS. 6 to 10 show an alternative embodiment of aerosol canister sleeve 100 which has all the same advantages as referred to the first embodiment of sleeve 10 referred to above. The second embodiment of sleeve 100 is formed of first and second parts 100*a/b*, which fit together by means of interengaging projections and tubes 102/104 respectively. The second embodiment holds an aerosol canister 14 (see FIG. 9) in position by means of ribs 106 of the first and second parts 100*a*/100*b* which engage a neck section 108 of the aerosol canister 14, which neck section 108 is formed just below the crimp section 18. Upward and downward movement of the aerosol canister relative to the sleeve 100 is prevented by engagement of the neck section 108 with the ribs 106. Further lateral movement is prevented by lower ribs 110/112. The second section 100*b* forms part of an outer surface of a spray device chassis 120. The second part 100*b* forms a continuous surface, matching the lines and contours of the chassis 120. Engagement of the sleeve 100 with the chassis 120 is by means of interengaging projections and recesses 114/116 (see FIG. 7). As shown in FIG. 10 a pocket 118 is provided for a magnet 42, which functions in the same manner as described above in relation to the first embodiment. The sleeve 100 has an opening 122 at a top part thereof, which is similar to the ring-shaped collar 26 of the first embodiment and allows the stem 28 of the aerosol canister 14 to project through a top of the sleeve 100.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A sleeve for a material container, the sleeve being adapted to receive a material container therein, the sleeve also being adapted to be received in an opening of a corresponding material ejection device chassis operable to control ejection of material from the material container,
   wherein a top end of the sleeve, when the sleeve is in an upright position, has an upwardly facing surface having a permanent magnet operable to activate an electromagnetic switch of the material ejection device chassis, wherein the sleeve is configured such that the permanent magnet located on the upwardly facing surface at the top end of the sleeve is located adjacent to the electromagnetic switch when the sleeve is inserted into the opening of the material ejection device chassis.

2. A sleeve as claimed in claim 1, which comprises one of a locating projection and recess pair(s), the other of the locating projection and recess pair(s) being part of the material ejection device chassis.

3. A sleeve as claimed in claim 1, which comprises material container gripping means, said material container gripping means comprising:
   first gripping elements comprising tabs facing generally in a first direction and adapted to engage a neck section of the material container, and
   second gripping elements adapted to extend over and adapted to engage a head section of the material container,
   wherein the first and second gripping elements are adapted to provide a snap fitting for the material container and are adapted to bear against the neck section and head section of the material container respectively.

4. A sleeve as claimed in claim 1, in which the electromagnetic switch is a reed switch.

5. A sleeve as claimed in claim 3, in which the magnet is located on the material container gripping means.

6. A sleeve as claimed in claim 1, in which the magnet is arranged so that poles thereof are generally aligned with a longitudinal axis of the sleeve.

7. A sleeve as claimed in claim 1, in which the magnet is located at or close to a vertex of the sleeve to allow the magnet to approach the electromagnetic switch.

8. A sleeve as claimed in claim 2, which comprises one of a locating projection and recess pair(s), the other of the locating projection and recess pair(s) being part of the material ejection device chassis.

9. A sleeve as claimed in claim 8, which incorporates the locating projection(s).

10. A sleeve as claimed in claim 9, in which the locating projection(s) extends along a body section of the sleeve.

11. A sleeve as claimed in claim 8, in which the locating projection(s) has a rounded profile.

12. A sleeve as claimed in claim 3, in which the second gripping elements are joined at upper ends thereof by a link section.

13. A sleeve as claimed in claim 12, in which the link section forms a ring adapted to engage the head section of the material container.

14. A sleeve as claimed in claim 1 incorporating a material container.

15. A pack containing a plurality of sleeves according to claim 1, in which each sleeve incorporates a material container.

* * * * *